United States Patent [19]
Naylor

[11] Patent Number: 5,519,154
[45] Date of Patent: May 21, 1996

[54] ETHOXYLATED ESTER SURFACTANTS AND A PROCESS THEREFOR

[75] Inventor: Carter G. Naylor, Austin, Tex.

[73] Assignee: Huntsman Corporation, Salt Lake City, Utah

[21] Appl. No.: 178,720

[22] Filed: Jan. 10, 1994

[51] Int. Cl.$^6$ ................................................ C07C 51/00
[52] U.S. Cl. ........................ 554/149; 554/92; 554/96; 554/97; 554/168
[58] Field of Search ........................... 554/92, 149, 96, 554/97, 168

[56] References Cited

U.S. PATENT DOCUMENTS

| | | | |
|---|---|---|---|
| 3,271,444 | 9/1966 | Percival et al. | 260/513 |
| 3,306,931 | 2/1967 | Adams et al. | 260/513 |
| 3,823,185 | 7/1974 | Schlossman | 260/513 B |
| 3,943,174 | 3/1976 | Ellis et al. | 260/513 B |
| 4,267,123 | 5/1981 | Chen et al. | 260/501.12 |
| 4,275,013 | 6/1981 | Tokosh et al. | 260/504 R |
| 4,442,042 | 4/1984 | Schmitt | 260/512 R |
| 4,954,282 | 9/1990 | Rys et al. | 252/117 |
| 5,232,633 | 8/1993 | Ilardi et al. | 252/554 |

FOREIGN PATENT DOCUMENTS 0544478  6/1993  European Pat. Off. .

OTHER PUBLICATIONS

S. C. Bright, et al., "Alkane Sulphonate Preparation by the sulphitation of Long Chain Olefins," *J. Appl. Chem. Biotechnol.*, 1975, vol. 25, pp. 901–912.
Chemical Abstract, 108:85254, 1988.

*Primary Examiner*—José G. Dees
*Assistant Examiner*—Deborah D. Carr
*Attorney, Agent, or Firm*—Russell R. Stolle; David L. Mossman

[57] ABSTRACT

A process for producing ethoxylated ester surfactants in high yield has been discovered which employs no halogen-containing reactants or intermediates. Allyl alcohol is reacted with ethylene oxide to give an allyl alcohol ethoxylate; the ethoxylate in turn is reacted with a bisulfite salt (e.g. sodium metabisulfite) to give an ethylene glycol propanesulfonate or polyethylene glycol propanesulfonate in high yield. The propanesulfonate is then reacted with a fatty acid to give the ethoxylated ester surfactant.

22 Claims, No Drawings

ETHOXYLATED ESTER SURFACTANTS AND A PROCESS THEREFOR

FIELD OF THE INVENTION

The invention relates to ethoxylated ester surfactants and processes for making the same, and, in one aspect, more particularly to methods for making ethoxylated ester surfactants in high yield with minimum by-products.

BACKGROUND OF THE INVENTION

A number of surfactants are known which are suitable for household cleaning products, personal care products, cosmetics, food emulsifiers and the like. However, many of the conventional surfactants are made by techniques which have intermediates that are formed in low yields making the overall process inefficient. Other preparatory methods use organo-halo intermediates which are often undesirable for potential toxicity and environmental reasons.

European Patent Application 0544478 A1 describes novel fatty acid esters of alkoxylated isethionic acid having the formula:

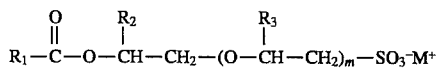

where $R_1$ is an alkyl group having 8 to 18 carbon atoms, m is an integer from 1–4, $R_2$ and $R_3$ are hydrogen or an alkyl group having 1–4 carbons, and $M^+$ is a monovalent cation, and compositions comprising these compounds. These esters are made by first preparing an alkoxylated isethionate via the sulfonation of a corresponding chloroalkoxy lower alcohol (e.g. 2-(2-chloroethoxy)ethanol) and subsequently treating the sulfoalkoxy lower alcohol (e.g. 2-(2-sulfoethoxy)ethanol) so formed with an alkoyl chloride where the alkoyl group has 8 to 18 carbons (e.g. lauroyl chloride) to form the above-mentioned ester. Note the presence of two halogenated intermediates.

Carbonated isethionate surfactants and methods for obtaining them are disclosed in U.S. Pat. No. 5,232,633. The surfactants have the formula:

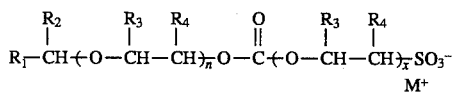

where n is a number from 0 to 10; x is 1 or 2; $R_1$ through $R_4$ inclusive may be independently hydrogen, aryl, cycloalkyl, alkylaryl, alkylene or straight or branched $C_{1-18}$ alkyl; and where $M^+$ is alkali metal, alkaline earth metal, ammonium or alkylammonium. These surfactants are made by reacting selected alcohols and alkoxyalcohols with phosgene followed by reactions with sodium isethionate. Phosgene is, of course, a very toxic chloride-containing gas; it would be desirable if its use could be avoided.

U.S. Pat. No. 4,275,013 discusses a process for the preparation of salts of alkanesulfonic acids, which are referred to as alkanesulfonates, by the addition of alpha olefins to bisulfite in a cosolvent system consisting of water and an organic hydroxyl-containing compound in the presence of a free radical initiator.

An improved process for producing ethoxylated isethionates in an aqueous medium is provided in U.S. Pat. No. 3,823,185. In the process, the selectivity of ethylene oxide to the desired ethoxylated products is significantly increased by removal of all or a substantial part of the water present in the early stages of the reaction after a small amount of ethylene oxide has reacted. Additionally, ethoxylated isethionates having from about 2 to about 30 ethylene oxide repeating units and containing less than 25% undesirable glycol by-products are provided.

A skin cleansing composition is provided that includes a combination of $C_{16}$–$C_{18}$ acyl isethionate ester salts having no more than 25% $C_{14}$ or lower acyl groups with at least one co-active surfactant according to U.S. Pat. No. 4,954,282. The weight ratio of acyl isethionate to co-active surfactant ranges from about 20:1 to about 1:1.

U.S. Pat. No. 4,267,123 describes an improved method for preparing propane sulfonates by the addition of metal bisulfites to allyl ethers, amines and sulfides, where a substantial amount of the desired product is added to the reaction mixture.

Three patents are known which relate to the reaction of bisulfite with olefins. U.S. Pat. No. 3,943,174 discloses a process for producing alkyl sulfonates by the addition of bisulfite ions to olefinic double bonds. In the process, ammonium, or an alkali metal bisulfite and olefins having from about 8–30 carbon atoms per molecule are reacted in the presence of a lower alkanol having from 2 to about 4 carbon atoms, water and a reaction initiating agent. A process for alkali metal bisulfite addition to primary olefins by means of a fast, continuous, one-phase air-initiated reaction system is discussed in U.S. Pat. No. 3,306,931, which uses a 2-propanol/water solvent combination in specific proportions. U.S. Pat. No. 3,271,444 relates to water-soluble salts of n-alkane-1,2-sulfonic-sulfinic acids having 10 to 20 carbon atoms, which are prepared by reacting n-olefins with a bisulfite salt in the presence of an alcohol solvent containing an organic tertiary-butyl perester.

An improved process for making propane sulfonates without isolating intermediates is discussed in U.S. Pat. No. 4,442,042 which involves (1) using an aqueous NaOH system instead of metallic sodium, and (2) recycling a portion of the product surfactant as a phase transfer catalyst to ensure intimate contact of the reactants. As in the process of U.S. Pat. No. 4,267,123, allyl halides are employed, which have toxicity concerns.

The free radical addition of sodium bisulphite to linear olefins (sulphitation) was investigated as described in S. C. Bright, et al., "Alkane Sulphonate Preparation by the Sulphitation of Long Chain Olefins," *J. Appl. Chem. Biotechnol.*, 1975, Vol. 25, pp. 901–912. The kinetic consequences of the probable mechanism of sulphitation were observed to be consistent with the experimental results.

It would be desirable to provide a process which does not require halogen-containing reactants or intermediates and which may also may be made in high yield without appreciable by-products.

SUMMARY OF THE INVENTION

Accordingly, it is an object of the present invention to provide a process for producing ethoxylated ester surfactants in high yield.

It is another object of the present invention to provide a method for making ethoxylated ester surfactants without the use of halogen-containing reactants or intermediates.

A particular object of the invention is to provide a way to produce ethoxylated ester surfactants that is relatively simple.

In carrying out these and other objects of the invention, there is provided, in one form, a process for making ethoxylated ester surfactants involving first reacting allyl alcohol with ethylene oxide to give an allyl alcohol ethoxylate. Secondly, the allyl alcohol ethoxylate is reacted with a bisulfite salt to give an ethylene glycol propanesulfonate. In the scope of this invention an "ethylene glycol propanesulfonate" is understood to encompass polyethylene glycol propanesulfonates, unless the material is termed EG-PS which designates a generally monoethylene glycol propanesulfonate. Finally, the ethylene glycol propanesulfonate is reacted with a fatty acid to produce the ethoxylated ester surfactants.

DETAILED DESCRIPTION OF THE INVENTION

A method of producing ethoxylates of 3-hydroxypropane sulfonic acid alkali metal salt, which form surfactants when condensed with fatty acids, has been discovered which produces the salts in high yield and without the use of halogen-containing reactants or intermediates. The resulting ethoxylated ester sulfonates are mild and effective in personal care and cleaning applications. The inventive process involves at least three steps:

(1) reacting allyl alcohol with ethylene oxide in the presence of a basic catalyst to produce an allyl alcohol ethoxylate;

(2) reacting the allyl alcohol ethoxylate with a bisulfite salt in the presence of a basic catalyst to form an ethylene glycol propanesulfonate; and (3) reacting the ethylene glycol propanesulfonate with a fatty acid by conventional means.

The ethoxylated ester surfactants produced by the invention may have the formula:

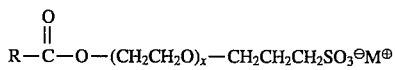

where R is a saturated or unsaturated straight or branched alkyl group averaging from about 6 to about 20 carbon atoms; x averages from about 1 to 10 and M is an alkali metal, calcium, ammonium, and the like.

The process of the invention may be schematically represented as follows in a non-limiting way:

First, allyl alcohol is reacted with the desired mole equivalents (x) of ethylene oxide to form an allyl alcohol ethoxylate:

$$CH_2=CH-CH_2-OH + xCH_2CH_2O \rightarrow CH_2=CH-CH_2-(OCH_2CH_2)_xOH$$

where x is defined as above. The value of x may average from about 1 to 10, preferably from about 1 to 3.

Secondly, the allyl alcohol ethoxylate is reacted with at least a mole equivalent of a bisulfite salt, here shown as an alkali metal (e.g. sodium) metabisulfite, in the presence of oxygen as initiator, to give a bisulfite addition product, which may also be referred to as a sulfonate:

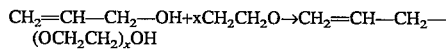

where M is defined as above. No separate organic hydroxyl-containing compounds or free radical initiators are used in this step.

In the third step, the bisulfite addition product is reacted with a fatty acid to give the ethoxylated ester surfactant in good yield:

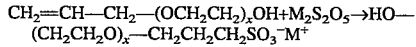

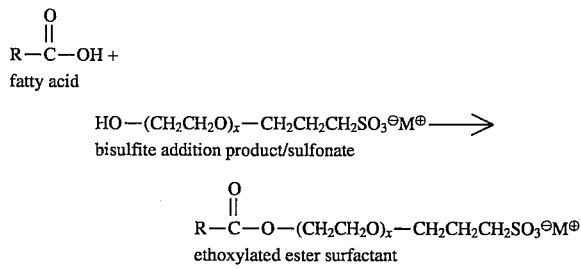

where R is as defined above.

Allyl Alcohol Ethoxylation

As noted, the mole equivalents of ethylene oxide to allyl alcohol may average from about 1 to about 10, preferably from about 1 to about 3. It is anticipated that other alcohols with terminal 1,2-unsaturation may be used in the practice of this invention, but allyl alcohol is highly preferred because of its availability and low cost. While other alkylene oxides may also be employed alone or together with ethylene oxide, they are less desired because they would adversely affect the hydrophilic properties of the anionic end of the product surfactant.

The ethoxylation of allyl alcohol is preferably conducted in the presence of a basic catalyst, which is preferably an alkali metal hydroxide such as NaOH, KOH or the like. The reaction may be conducted at a temperature ranging from about 80° to about 180° C. The reaction should be conducted to consume all of the ethylene oxide. It will be desirable to neutralize the catalyst and to distill off any unreacted allyl alcohol prior to proceeding. Other catalysts may be used which narrow the distribution of ethoxylate oligomers, such as Lewis acids (including, but not necessarily limited to $SnCl_4$, $BF_3$, $ZnCl_2$, etc.) and alkali earth metal hydroxides and oxides.

Sulfonation

The allyl alcohol ethoxylate produced by the first step is next reacted with a bisulfite salt in the presence of oxygen as a free radical initiator. Appropriate alkali metal bisulfites may include but are not limited to sodium bisulfite, sodium metabisulfite, potassium bisulfite, potassium metabisulfite, ammonium bisulfite, calcium bisulfite, and the like. The combination of sulfur dioxide and sodium hydroxide may be used as a source of sodium bisulfite; indeed, this is the bisulfite source that would probably be used in a commercial facility. At least one mole equivalent of bisulfite relative to the allyl alcohol ethoxylate is required. Water is a preferred solvent. The pH should be buffered to between about 6.0 and about 7.8, as desired, prior to starting the reaction by addition of hydroxide and $SO_2$ or bisulfite. The reaction begins when oxygen (or air) is introduced.

The sulfonation reaction may be conducted at a temperature from about 25° to about 90° C., preferably from about 50° to about 70° C. These conditions are relatively mild. The yield of the sulfonate (bisulfite addition product) is unusually good, often at least 90%, commonly at least 95%, even quantitative. One technique for improving yield is the incremental addition of the glycol ether. The sulfonate product can be used as-is, without isolation prior to the reaction with the fatty acid.

Ester Surfactant Preparation

The sulfonate of the second step is reacted with a fatty acid which may be saturated or unsaturated, straight or branched having from about 6 to about 20 carbon atoms. The fatty acid may be a single fatty acid, or may be a mixture or blend of different fatty acids, in which case the mixture of fatty acids has an average of from about 6 to about 20 carbon atoms. Suitable fatty acids include, but are not necessarily limited to, coconut fatty acid, lauric acid, palmitic acid, stearic fatty acid, oleic acid, linoleic acid, linolenic acid, palm kernal fatty acid, tall oil fatty acid, and the like. At least one mole equivalent of fatty acid to the sulfonate should be used; in one embodiment, preferably at least 1.3 mole equivalent should be employed.

The reaction temperature may range from about 180° to about 250° C., preferably from about 200° to about 240° C. In one embodiment, the sulfonate may be added dropwise or incrementally as the aqueous solution to the fatty acid at about 180° C. After addition, digestion may follow at a temperature from about 210° to about 240° C. This last step is conventional and has not been optimized in the present Examples. Yields as high as 95% or higher are anticipated. The R group, of course, provides the hydrophobic portion of the surfactant.

The method and products of this invention will be illustrated by the following Examples which are not limiting of the invention but merely set it out in further detail.

EXAMPLE 1

A. Preparation and Distillation of Allyl Alcohol Ethoxylate

Allyl alcohol was ethoxylated using potassium hydroxide catalyst and 1.5 equivalents of ethylene oxide. Gas chromatography (GC) analysis indicated 4% unreacted allyl alcohol, 23% monoethoxylate, 32% diethoxylate, 23% triethoxylate and the balance higher oligomers. The first two components were distilled off at atmospheric pressure up to 168° C. The desired component, the diethoxylate, was distilled under vacuum (115°–120° C. at 8 torr). It was 98% pure by GC analysis.

B. Sulfonation of Allyl Alcohol Diethoxylate

The glycol ether prepared above, 100 g=685 meq, was mixed with 150 g water and 6.0 g 50% sodium hydroxide. A 33.3 wt. % solution of sodium metabisulfite was added until the pit reached 7.2. The mixture was heated to 60° C., then air was bubbled in at 10 ml/min. The metabisulfite solution (3.5 meq/g) was added at a rate which maintained pH at 7.2. After 8 hours, a total of 233 g was consumed.

Analysis by high pressure liquid chromatography (HPLC) showed no residual glycol ether, a single product peak and two peaks attributed to inorganic sulfate and sulfite salts. This product is diethylene glycol propanesulfonate (DEG-PS).

EXAMPLE 2

Preparation of Ethylene Glycol Propanesulfonate (EG-PS)

The glycol ether, allyloxyethanol, was distilled from the allyl alcohol ethoxylate (see Example 1.A.) at atmospheric pressure and 154°–162° C. GC analysis indicated purity of 98%.

It was mixed with water (50 g with 150 g) and 4.0 g 50% sodium hydroxide. Sodium metabisulfite solution (38 wt. %, 4.0 meq/g) was added to adjust the pH to 7.2. Then, at 60° and 15 ml/min. air flow into the reaction solution, metabisulfite was added at a rate sufficient to maintain pH at 7.2 for 2 hours. By then 128.0 g had been consumed.

Analysis of the product by HPLC indicated 95% product, not counting the inorganic compounds. Also present was 1% nonionic starting material and 4% of two by-products.

EXAMPLE 3

Preparation of Triethylene Glycol Propanesulfonate

Triethylene glycol mono-allyl ether was distilled from the ethoxylate of allyl alcohol (see Example 1.A.) under vacuum (104°–108° C. at 0.2 torr). GC analysis indicated 97% purity.

This glycol ether was sulfonated by the same procedure noted in Example 1.B. and Example 2 except on a larger scale. 900 g water, 300 g ether and 20 g 50% sodium hydroxide at 60° C. were reacted with aqueous sodium metabisulfite at pH 7.2 in 2.5 hours.

HPLC analysis showed 88% major product, 2% ether and 10% due to two by-products.

Examples 1–3 illustrate the mild conditions needed for this high yield reaction of sulfonating allyl glycol ethers. Distilling the allyl alcohol ethoxylate into fractions for the various Examples demonstrates that the sulfonation can be performed with a variety of ethoxylates. Of course, the allyl alcohol ethoxylate may sulfonated without distilling into its various fractions. The following Examples show the range of conditions which may be used for the sulfonation.

EXAMPLE 4

Preparation of Ethylene Glycol Propanesulfonate (EG-PS)

The allyl glycol ether of Example 2, 50 g, was mixed with 50 g water and 2.0 g 50% sodium hydroxide. Sodium metabisulfite solution (38 wt. %) was added to adjust the pH to 6.4, the reaction mixture was heated to 50° C., and air bubbled into the mixture at 25 ml/min. A total of 142.6 g metabisulfite solution was added. HPLC analysis showed 80% product, 18% by-product and 1% unreacted ether.

EXAMPLE 5

Preparation of Diethylene Glycol Propanesulfonate (DEG-PS)

Allyloxyethoxyethanol, the diethoxylate of allyl alcohol, 50 g, was mixed with 150 g water, 6.0 g 50% sodium hydroxide, heated to 70° C. and neutralized to pH 7.8 with 38% sodium metabisulfite solution. Air was then bubbled through the reaction mixture at 25 ml/min. and metabisulfite added to maintain the pH at 7.8 over two hours. A total of 71.1 g metabisulfite solution was added. HPLC analysis gave 19% unreacted ether, 80% DEG-PS product and 1% by-product.

Examples 4 and 5 indicate that the desire pH range for maximizing yield of sulfonate and minimizing by-products is above about 6.4 and below about 7.8. Temperature, air flow rate, amount of sodium hydroxide and water are less critical.

A technique for improving yield in one embodiment is incremental addition of the glycol ether rather than having it all in the reaction vessel initially. The following two Examples are illustrative.

EXAMPLE 6

Incremental Addition of Glycol Ether

Allyl alcohol diethoxylate, 10 g, was mixed with 100 g water and 4.0 g 50% sodium hydroxide and heated to 60° C. The pH was adjusted to 7.2 with metabisulfite solution and air flow at 15 ml/min. begun. Every thirty minutes a 10 g increment of the ether was added up to a total of 50 g after two hours. The reaction was complete in 2.75 hours, by which time 259.9 g metabisulfite had been added. HPLC analysis showed no ether, 97% DEG-PS product and 3% by-products.

EXAMPLE 7

Counter Example to Example 6

The same procedure as Example 6 was followed, except that all 50 g of glycol ether was added at once initially. After two hours, the reaction was complete; a total of 101.6 g metabisulfite solution had been added. HPLC showed 92% product, 1% ether and 6% by-products. The by-products seen by HPLC were identified by NMR analysis.

EXAMPLE 8

NMR Analysis of DEG-PS

The DEG-PS product prepared in Example 7 was analyzed by $^{13}$C NMR which revealed the following:

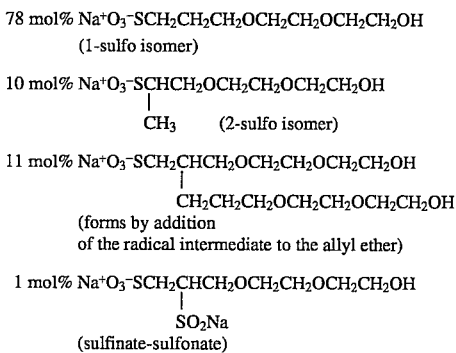

78 mol% $Na^+O_3^-SCH_2CH_2CH_2OCH_2CH_2OCH_2CH_2OH$
(1-sulfo isomer)

10 mol% $Na^+O_3^-SCHCH_2OCH_2CH_2OCH_2CH_2OH$
 | 
 $CH_3$ (2-sulfo isomer)

11 mol% $Na^+O_3^-SCH_2CHCH_2OCH_2CH_2OCH_2CH_2OH$
 | 
 $CH_2CH_2CH_2OCH_2CH_2OCH_2CH_2OH$
(forms by addition
of the radical intermediate to the allyl ether)

1 mol% $Na^+O_3^-SCH_2CHCH_2OCH_2CH_2OCH_2CH_2OH$
 | 
 $SO_2Na$
(sulfinate-sulfonate)

The first two compounds were not resolved by HPLC. Peak assignments for the other two components were not made. The compounds other than the 1-sulfo isomer are acceptable as part of the product because they are also sulfonates which can form ester surfactants.

EXAMPLE 9

Preparation of Coconut Acid Ester of EG-PS

An aqueous solution of ethylene glycol propanesulfonate produced in Example 2 had about 33 wt. % active concentration and NMR assay of 92 mol % 1-sulfo isomer, 2 mol % 2-sulfo isomer, 5 mol % radical addition product and 1–2 mol % sulfinate-sulfonate. A 190 g portion was treated with 2.5 g 30% hydrogen peroxide to consume the excess bisulfite and 1.3 g sodium hydroxide to raise the pH to 8.

The EG-PS solution (approximately 0.74 mole equivalent) was added dropwise to 80 g coconut fatty acid (Emery 626 acid from Emery Industries, Inc.) and 3 g of coco zinc soap in coco acid (3.8 wt. % Zn) as a catalyst at 180° C. The addition took 1.5 hours and the water was distilled out. The mixture, now a smooth dispersion, was digested at 230° C. for 3 hours. Analysis by titration for anionic surfactant was 0.58 meq/g, indicating 28% yield of surfactant product.

EXAMPLE 10

Preparation of DEG-PS Coconut Ester

The same procedure as in Example 9 was followed, except that DEG-PS was used from Example 6. The yield was 43% coco ester of DEG-PS.

EXAMPLE 11

Preparation of TEG-PS Coconut Ester

The same procedure as in Example 9 was followed, except that TEG-PS was used from Example 3 The yield was 88% coco ester of TEG-PS.

Examples 9–11 demonstrate that the propanesulfonates can be converted to surfactant derivatives by conventional means, although the reaction conditions are not optimized for the highest yield to the ester.

EXAMPLE 12

Demonstration of Surfactant Activity

Solutions of ethoxylated ester sulfonates, made according to the procedures of Examples 9, 10 and 11, were prepared in 0.1% concentrations in hard water (140 ppm as $CaCO_3$, 2:1 Ca:Mg molar ratio). Table I summarizes wetting times (Draves cotton skein test at 25° C.), foam heights (Ross-Miles test at 49° C.), and surface tension at 25° C.

TABLE I

| | Surfactant Activity | | | | |
|---|---|---|---|---|---|
| | Wetting Time, sec. | | Foam Height, mm | | Surface Tension |
| Coco Ester | 1.5 g hook | 3 g hook | initial | 5 min. | dynes/cm |
| EG-PS | 45 | 25 | 139 | 139 | 27.0 |
| DEG-PS | 47 | 28 | 124 | 62 | 29.2 |
| TEG-PS | 81 | 51 | 134 | 134 | 28.8 |

Many modifications may be made in the process of this invention without departing from the spirit and scope thereof which are defined only in the appended claims. For example, one skilled in the art may discover that particular reaction conditions, sequences, and reactants give ethoxylated ester surfactants with particularly advantageous properties or yields, which may not be explicitly recited herein, but are nevertheless anticipated.

I claim:

1. A process for making ethoxylated ester surfactants comprising the steps of:
   (a) reacting allyl alcohol with from about 1 to about 10 mole equivalents of ethylene oxide in the presence of a catalyst selected from the group consisting of alkali metal hydroxides, alkali earth metal oxides, alkali earth metal hydroxides, and Lewis acids, to give an allyl alcohol ethoxylate;
   (b) reacting the allyl alcohol ethoxylate with a bisulfite salt selected from the group consisting of sodium bisulfite and sodium metabisulfite in the presence of oxygen and a buffered aqueous solution at a temperature in the range of about 25° to about 90° C. and are reacted at pH of between about 6.0 and about 7.8, where the mole ratio of bisulfite salt to allyl alcohol ethoxylate is at least 1:1, to give an ethylene glycol propanesulfonate in at least 95% yield; and (c) reacting the ethylene glycol propanesulfonate with at least one fatty acid selected from the group consisting of fatty acids which are saturated or unsaturated, straight or branched, and have from about 6 to about 20 carbon atoms, at a temperature in the range of about 180° to about 250° C.

2. A process for making ethoxylated ester surfactants comprising the steps of:

(a) reacting allyl alcohol with from about 1 to about 10 mole equivalents of ethylene oxide to give an allyl alcohol ethoxylate;

(b) reacting the allyl alcohol ethoxylate with a bisulfite salt selected from the group consisting of sodium bisulfite, sodium metabisulfite, and a combination of sulfur dioxide and sodium hydroxide, to give an ethylene glycol propanesulfonate in at least 95% yield; and (c) reacting the ethylene glycol propanesulfonate with at least one fatty acid selected from the group consisting of fatty acids which are saturated or unsaturated, straight or branched, and have from about 6 to about 20 carbon atoms.

3. The process of claim 2 where in step (b) the reacting of allyl alcohol with ethylene oxide is conducted in the presence of a catalyst selected from the group consisting of alkali metal hydroxides, alkali earth metal oxides, alkali earth metal hydroxides, and Lewis acids.

4. The process of claim 2 where in step (b) the mole ratio of bisulfite salt to allyl alcohol ethoxylate is at least 1:1, and where the bisulfite salt and the allyl alcohol ethoxylate are reacted in the presence of oxygen and a buffered aqueous solution at a temperature in the range of about 25° to about 90° C. and are reacted at pH of between about 6.0 and about 7.8.

5. The process of claim 2 where in step (c) the reacting of ethylene glycol propane sulfonate with fatty acid is conducted at a temperature in the range of about 50° to about 70° C.

6. A process for making ethoxylated ester surfactants comprising the steps of:

(a) reacting allyl alcohol with ethylene oxide to give an allyl alcohol ethoxylate;

(b) reacting the allyl alcohol ethoxylate with a bisulfite salt to give an ethylene glycol propanesulfonate; and (c) reacting the ethylene glycol propanesulfonate with at least one fatty acid.

7. The process of claim 6 where in step (a) the proportion of ethylene oxide ranges from about 1 to about 10 mole equivalents of allyl alcohol.

8. The process of claim 6 where in step (b) the bisulfite salt is selected from the group consisting of sodium bisulfite, sodium metabisulfite, and a combination of sulfur dioxide and sodium hydroxide.

9. The process of claim 6 where in step (c) the fatty acid is selected from the group consisting of fatty acids which are saturated or unsaturated, straight or branched, and have from about 6 to about 20 carbon atoms.

10. The process of claim 6 where the yield to the ethylene glycol propanesulfonate in step (b) is at least 90%.

11. The process of claim 6 in the absence of halogen-containing reactants.

12. The process of claim 6 where in step (a) the reacting of allyl alcohol with ethylene oxide is conducted in the presence of a catalyst selected from the group consisting of alkali metal hydroxides, alkali earth metal oxides, alkali earth metal hydroxides, and Lewis acids.

13. The process of claim 6 where in step (b) the mole ratio of bisulfite salt to allyl alcohol ethoxylate is at least 1:1, and where the alkali metal sulfite and the allyl alcohol ethoxylate are reacted in the presence of oxygen at a temperature in the range of about 25° to about 90° C. and are reacted at pH of between about 6.0 and about 7.8.

14. The process of claim 6 where in step (c) the reacting of ethylene glycol propane sulfonate With fatty acid is conducted at a temperature in the range of about 180° to about 250° C.

15. Ethoxylated ester surfactants having the composition:

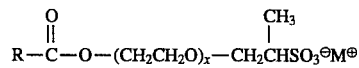

where R is a saturated or unsaturated straight or branched alkyl group averaging from about 6 to about 20 carbon atoms; x averages from about 1.0 to 10 and M is an alkali metal.

16. The ethoxylated ester surfactants of claim 15 where R averages from about 8 to about 18 carbon atoms and x averages from about 1 to about 3.

17. The ethoxylated ester surfactants of claim 15 produced by a process comprising the steps of:

(a) reacting allyl alcohol with from about 1 to about 10 mole equivalents of ethylene oxide to give an allyl alcohol ethoxylate;

(b) reacting the allyl alcohol ethoxylate with a bisulfite salt to give an ethylene glycol propanesulfonate; and (c) reacting the ethylene glycol propanesulfonate with at least one fatty acid.

18. The ethoxylated ester surfactants of claim 17 where the alkali metal sulfite in the process is selected from the group consisting of sodium bisulfite, sodium metabisulfite, and a combination of sulfur dioxide and sodium hydroxide.

19. The ethoxylated ester surfactants of claim 17 where the fatty acid in the process is selected from the group consisting of fatty acids which are saturated or unsaturated, straight or branched, and have from about 6 to about 20 carbon atoms.

20. Ethoxylated ester surfactants having the composition:

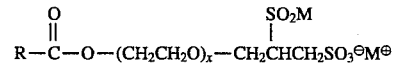

where R is a saturated or unsaturated straight or branched alkyl group averaging from about 6 to about 20 carbon atoms; x averages from about 1.0 to 10 and M is an alkali metal.

21. Ethoxylated ester surfactants having the composition:

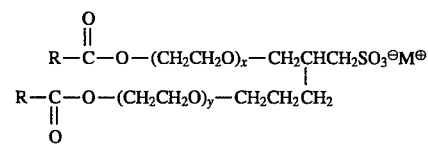

where R is a saturated or unsaturated straight or branched alkyl group averaging from about 6 to about 20 carbon atoms; x and y independently average from about 1.0 to 10 and M is an alkali metal.

22. A mixture of ethoxylated ester surfactants selected from the group having the composition:

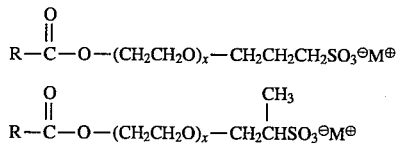

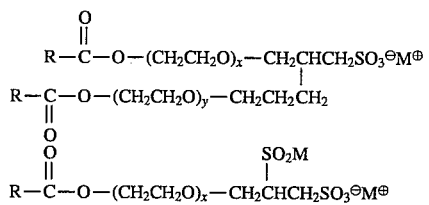

where R is a saturated or unsaturated straight or branched alkyl group averaging from about 6 to about 20 carbon atoms; x and y independently average from about 1.0 to 10 and M is an alkali metal.

* * * * *